United States Patent [19]

Berg

[11] 4,387,240

[45] Jun. 7, 1983

[54] OLIGOMERIC METHACRYL SUBSTITUTED ALKYLSILOXANES

[75] Inventor: Eric P. Berg, Woodbury, Minn.

[73] Assignee: Minnesota Mining and Manufacturing Company, Saint Paul, Minn.

[21] Appl. No.: 911,892

[22] Filed: Jun. 2, 1978

[51] Int. Cl.$^3$ .............................................. C07F 7/18
[52] U.S. Cl. .................................... 556/440; 556/460
[58] Field of Search ................................ 260/448.8 R

[56] References Cited

U.S. PATENT DOCUMENTS 3,878,263  4/1975  Martin ...................... 260/448.2 Q X
4,026,826  5/1977  Yoshida et al. .......................... 260/2
4,153,641  5/1979  Deichert et al. ......... 260/448.2 Q X

FOREIGN PATENT DOCUMENTS 949126  2/1964  United Kingdom ........ 556/440 UX

Primary Examiner—Paul F. Shaver
Attorney, Agent, or Firm—Cruzan Alexander; Donald M. Sell; Robert W. Sprague

[57] ABSTRACT

Oligomers of highly purified methacryl substituted silanes, e.g., methacryloxyalkyltrialkoxysilanes, can be combined with (meth)acrylate monomers to give viscosities in a range such that they can be heavily filled for use in dental filling compositions. They can remain stable for extended times in contact with catalyst until initiated and are of particular value in two part dental filling systems.

4 Claims, No Drawings

OLIGOMERIC METHACRYL SUBSTITUTED ALKYLSILOXANES

This invention relates to oligomeric methacryl substituted alkylsiloxanes and particularly to oligomeric methacryloxyalkylsiloxanes. This invention further relates to dental restorative or filling compositions having binders comprising polymerized methacryloxyalkylsiloxanes.

The art of filling teeth to replace metallic fillings by polymeric fillings has advanced greatly in recent years. There has been considerable success in the fields of gingival and anterior fillings where little abrasion is encountered but occlusal fillings in particular remain difficult to supply because of the excessively abrasive conditions, e.g., during mastication. Composite materials have generally been found to be unsatisfactory as occlusal fillings because of their lack of abrasion resistance. It is accordingly a principal aim and object of this invention to provide dental filling compositions having improved abrasion resistance. Other objects will appear from the reading of the present disclosure.

It has been found that oligomeric methacryloxyalkylsiloxanes are valuable binders in dental filling compositions and that, when properly composed, they are stable for prolonged periods and can then polymerize rapidly to give abrasion resistant fillings.

Silane compounds for use with various acrylates are enumerated extensively by Yoshida and Kaetsu in U.S. Pat. No. 4,026,826. Examples show that certain such materials provide useful abrasion-resistant coatings when polymerized by irradiation with γ-rays for prolonged periods together with greater or less heating periods. Such conditions would be entirely unacceptable for dental practice and would not leaad one to search such materials for dental purposes. It is therefore surprising that it has been found that methacryl substituted alkyltrialkoxysilanes which are usually of an amber color can be freed from normally occurring inhibitors and other impurities and obtained as water-white stable liquids substantially free from inhibitors and numerous fortuitous contaminants and that such purified methacryl substituted alkyltrialkoxysilanes are converted to oligomeric prepolymers, e.g., methacryloxyalkylsiloxanes, by hydrolysis with acidified water. The resulting colorless prepolymer can be combined with from 0 to 50% (meth)acrylic monomers to provide colorless liquid compositions having viscosities in the range of about 1000 to about 30,000 centipoises which are highly useful in dental compositions. These compositions can be polymerized with free radical catalysts at greatly increased speeds under ambient conditions to give substantially colorless highly cross-linked polymers. The term (meth)-acrylate is intended to refer to both acrylates and methacrylates. It is further found that these compositions of oligomeric prepolymers, with or without (meth)acrylate comonomers, can incorporate substantial amounts, about 60-85% by weight, of various fillers and further can be formulated as two part dental systems which provide outstandingly abrasion-resistant dental fillings.

It is found that commercial and heretofore available methacryl substituted alkyltrialkoxysilanes are so grossly contaminated with numerous impurities, inhibitors, etc., that they are entirely unsuited for the present purposes. When freed from these impurities they are substantially new compounds in their properties. A particularly useful procedure for removal of impurities involves successive treatments with mild and strong bases which might be expected to be destructive. Exemplary steps of a preferred process are:

A. First, the silane is stirred at about 130° C. with 10% anhydrous sodium carbonate for about 4 hours;

B. Second, the silane is separated and cooled to about 20° C. and about 0.15% potassium hydroxide is added and the suspension stirred at about 20° C. for about 1 hour;

C. Lastly, the silane is separated from residual potassium hydroxide and distilled under vacuum (preferably below 10 mm Hg pressure) to give a water-white stable liquid methacryl substituted alkyltrialkoxysilane freed from contaminants and inhibitors to the extent that an exotherm with substantial increase in viscosity or gelation occurs in 20 minutes at ambient temperatures after thorough mixing of approximately equal portions to which have been added, respectively, 1.5% by weight benzoyl peroxide and 3.0% by weight N,N-bis(hydroxyethyl)-p-toluidine. A substantial increase in viscosity is recognized as at least fivefold increase in viscosity.

It will be recognized that some variations in the purification process are permissible such as the use of other anhydrous non-nucleophilic bases such as carbonates, e.g., $K_2CO_3$, $Na_2CO_3$, or other massive, e.g., pelletted, nucleophilic inorganic bases such as $Ba(OH)_2$, $NaOH$. One might expect that treatment with a strong base such as potassium hydroxide would catalyze hydrolysis of the ester (i.e. alkoxy) groups and result in premature polymerization. It is surprising that no significant occurrence of such side-reactions is observed.

Hydrolysis of purified methacryl substituted alkyltrialkoxysilane is conveniently effected in a purified solvent such as tetrahydrofuran or methanol using an acid and water, preferably an acid such as 1 N hydrochloric acid, in an amount of about 20% and a trace (about 0.02 percent) of butylated hydroxy toluene. The solvent medium used for hydrolysis should be free from significant impurities and soluble in or miscible with water, at least in the presence of water soluble solvents. Suitable purified solvents include propanol, methanol, methyl ethyl ketone, ethanol, tetrahydrofuran and dioxane.

The combination is refluxed for about one hour and solvent, water and alcohol formed by hydrolysis are then removed under reduced pressure followed by purging with air to remove residual HCl. The water-white residue has a viscosity of about 5,000 to about 30,000 centipoises and is suitable for compositions for dental fillings.

Suitable methacryl substituted alkyltrialkoxysilanes are of the general formula

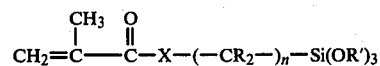

wherein
X is O, S or NR,
n is 3 to 12,
each R is independently hydrogen or lower alkyl of 1 to 2 carbon atoms and no more than two are lower alkyl,
R' is unsubstituted lower alkyl of 1 to 4 carbon atoms.

Exemplary compounds include:

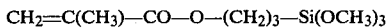

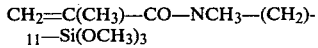

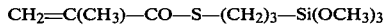

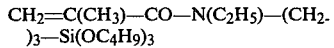

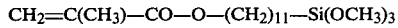

The oligomeric prepolymer is found by nuclear magnetic resonance spectroscopy to have a structure represented by

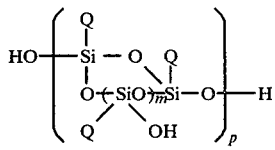

where
Q is $CH_2=C(CH_3)CO-X(CR_2)_n-$ where
X, R and n are as defined above and each m is independently 1, 2 or 3 and
p is 2 to about 10.

Suitable comonomeric acrylates and methacrylates include the following mono and bis acrylates: Acrylic acid, methacrylic acid, ethyl acrylate, methyl acrylate, propyl acrylates, butyl acrylates, methyl methacrylate, ethyl methacrylate, propyl methacrylates, butyl methacrylates, hydroxyethyl methacrylate, hydroxypropyl methacrylate, 2-ethylhexyl methacrylate, cyclohexyl acrylate, acrylamide, methacrylamide, acrylonitrile, methacrylonitrile, ethyleneglycol diacrylate, ethylene glycol dimethylacrylate, diethylene glycol diacrylate, diethylene glycol dimethylacrylate, triethylene glycol diacrylate, triethylene glycol dimethacrylate, tetraethylene glycol diacrylate, tetraethylene glycol dimethacrylate, 2,2'-propane bis[3(4-phenoxy)-1,2-hydroxy propane-1-methacrylate], and other similar components.

The oligomeric prepolymers and comonomeric acrylates to methacrylates are used in amounts of 5-100% and preferably 50-100% oligomeric prepolymers and 95-0% and preferably 50-0% acrylates or methacrylate comonomers. A particularly preferred range is from 90-95% oligomeric prepolymer with from 10 to 5% (meth)acrylate comonomer.

Compositions of the invention polymerize readily under the influence of free radical catalysts or initiators capable of initiating radically polymerizable monomers such as peroxides, hydroperoxides, dinitriles, redox catalyst systems, etc. Specific catalysts include benzoyl peroxide, methyl ethyl ketone peroxide, tertiary butyl hydroperoxide and tertiary butyl perbenzoate. Such initiators may be used with various activators, preferably aromatic amines, or may be activated thermally.

Compositions of the invention are also polymerized rapidly by exposure to light of wavelengths shorter than 500 nm, e.g., ultraviolet light, when they contain known free radicals forming aromatic ketonic initiator, such as benzoins, acetophenones, aromatic diketones, etc. with or without appropriate aliphatic amine accelerators such as dimethylaminoethyl methacrylate, triethanolamine. Such compositions form useful one-part systems which are generally stable to ambient light conditions.

Useful representative activators which are desirably added, include accelerators such as N,N-bis(hydroxyethyl)-p-toluidine, N,N-dimethyl-p-toluidine, N,N-bis(hydroxylower alkyl)-3,5-xylidines, p-toluenesulfinic acid, 1,3,5-trimethyl barbituric acid, 1-benzyl-5-phenyl-barbituric acid and 5-butyl barbituric acid. For two part systems which polymerize readily when mixed the composition is used in two portions one of which includes the accelerator and the other includes the peroxide catalyst. The polymerizing composition should contain about 0.5 to about 2 percent by weight of catalyst and about 1 to about 3 percent by weight of accelerator. The concentration in the respective parts are so adjusted that predetermined amounts of each are mixed immediately before polymerization is to be initiated and polymerization then occurs in about 0.5 to 10 minutes. Similar amounts of initiator and up to about 3% accelerator are used for UV-polymerizable one-part systems which polymerize very rapidly (from a few seconds to about 1 minute) on exposure to light of less than 500 nm wavelength.

For dental fillings it is usual to include inorganic nonmetallic fillers in amounts of 60 to 85% by weight in each portion of the composition. Such fillers include ground quartz, amorphous or fumed silicas, barium-containing glasses, aluminum oxide, glass beads, fused silicas and ground glasses comprising compounds of lanthanum, hafnium, strontium or tantalum. A presently preferred filler is quartz powder of about 8 micron average particle size. In general particles are used of sizes between about 0.001 and 40 microns and combinations of filler particles within this range. Pigments and radio-opaque materials are also included in dental restoratives as part of the fillers as is conventional in the art.

Some fillers can be employed without surface treatment but somewhat better wetting of filler particles is attained when the latter are treated with γ-methacryloxypropyltrimethoxysilane or vinyltriethyoxysilane in the manner which has become relatively conventional for dental filling compositions. The former is used in the examples.

The invention is now further illustrated by the following examples in which parts are by weight unless otherwise indicated.

EXAMPLE 1

A flask of about 2 l. capacity in a heating mantle and fitted with reflux condenser, mechanical stirrer and thermometer is charged with 1500 g of amber-colored commercial γ-methacryloxypropyltrimethoxysilane (available from Union Carbide as A-174 or from Dow Corning as Z-6030) and 150 g anhydrous sodium carbonate. The flask and contents are heated to about 130° C. and maintained at that temperature with stirring for 4 hours. The mixture is cooled to ambient temperature, filtered to remove the insoluble residue and the filtrate returned to the flask together with about 2.25 g (0.15%) potassium hydroxide pellets. Stirring is maintained for 1 hour without heating as the liquid becomes very dark brown to black in color. The liquid is decanted and distilled under vacuum at 85°–100° C. and 1–5 mm Hg (or torr) pressure to yield water-white γ-methacryloxypropyltrimethoxysilane which is characterized by being substantially free from inhibitors and polymerizing to substantially increased viscosity or gelation within less than 20 minutes at 15°–25° C. when activated by 1.5% benzoyl peroxide and 3% N,N-bis(hydroxyethyl)-p-toluidine activator. Under similar conditions the amber-colored commercial materials shows no indication of increase in viscosity after weeks of standing. It is substantially nonpolymerizable under these test conditions.

A flask is charged with 150 g of the above purified γ-methacryloxypropyltrimethoxysilane, 150 ml of tetrahydrofuran (analytical reagent grade) 0.03 g butylated hydroxytoluene (as a stabilizer) and 33.6 g 1 normal hydrochloric acid. The mixture is refluxed for one hour and then evaporated in vacuum (45° C. at ≦5 mm Hg) to provide a residue of water-white clear oligomeric prepolymer, i.e., methacryloxypropylpolysiloxane, having a viscosity of about 11,000 cps after air-purging. This material is employed in dental compositions as described below. There are about 0.30 hydroxyl groups per silicon atom.

EXAMPLE 2

A two part dental restorative system is prepared using the above oligomeric prepolymer:
Part A
  Prepolymer—20.0 parts
  Benzoyl peroxide—0.30 part
  Butylated hydroxytoluene—0.004 part
  Bisphenol A (food grade)—0.024 part
Part B
  Prepolymer—20.0 parts
  N,N-bis(hydroxyethyl)-p-toluidine—0.60 part
  2-(2'-hydroxy-5'-methylphenyl)-benzotriazole—0.1 part Each part is mixed thoroughly and about 60 parts of silane-treated ground crystalline quartz filler of about 8 micron average particle size is incorporated into each of Parts A and B by shaking in a paint mixer until pastes of uniform consistency are obtained.

A sample of material is polymerized by combining approximately equal amounts of Parts A and B by mixing together with a spatula. The composition cures to a hard mass within about 3 minutes from the time mixing is started. These two parts are stable for prolonged periods of months when not mixed and can be included in predetermined amounts as parts of a kit for use by dentists. When mixed they are then effective as restorative compositions for filling cavities in teeth and have remained essentially unchanged for over twelve months as posterior occlusal fillings in human teeth.

EXAMPLE 3

A further two part system is prepared in which Part A is as in Example 2 above. Part B is prepared from
  7.5 parts—bisphenol A diglycidyl ether bismethacrylate (prepared as described in U.S. Pat. No. 3,066,112)
  2.5 parts—triethylene glycol bismethacrylate
  0.15 part—N,N-bis(2-hydroxyethyl)-p-toluidine
  30.0 parts—powdered quartz (as used in Example 2)

Equal amounts of Parts A and B are mixed as in Example 2 and a hard resin is obtained in approximately two minutes at room temperature. There is no significant exotherm during the reaction. The separate parts are stable and do not polymerize when stored for periods of months.

EXAMPLE 4

Comparisons are made between composite restorative compositions containing the prepolymer of the invention as in Examples 2 and 3 (designated II and III respectively) and a dental filling composition (not according to this invention, designated I) in which both parts contain the methacrylates of Part B of Example 3. In each case 75 parts quartz powder as in the above examples is combined with 25 parts of the following compositions.

TABLE 1

|  | Part A | | | Part B | | |
| --- | --- | --- | --- | --- | --- | --- |
|  | I | II | III | I | II | III |
| Bisphenol A diglycidyl ether bismethacrylate | 75 | — | — | 75 | — | 75 |
| Triethylene glycol bis-methacrylate | 25 | — | — | 25 | — | 25 |
| Prepolymer of Example 1 | — | 100 | 100 | — | 100 | — |
| Benzoyl peroxide | 1.14 | 1.5 | 1.25 | — | — | 2.2 |
| N,N—bis(hydroxyethyl)-p-toluidine | — | — | — | 2.2 | 3 | 2.2 |

These compositions harden readily in 2±0.25 minutes when mixed in equal amounts. Cured samples are prepared and compared for hardness using a Barcol Impressor (standard testing machine available from Barber Coleman Co.) at times of 5 minutes to 24 hours after initiating mixing as given in Table 2.

TABLE 2

|  | Composition | | |
| --- | --- | --- | --- |
| Time | I | II | III |
| 5 | 74 | 70 | 78 |
| 8 | 78 | 74 | 82 |
| 10 | 78 | 75 | 83 |
| 15 | 79 | 78 | 84 |
| 20 | 79 | 80 | 85 |
| 30 | 80 | 82 | 86 |
| 60 | 80 | 84 | 88 |
| 1440 | 84 | 90 | 90 |

The results show that compositions containing 50% or more of the acryloxyalkyloxysiloxane prepolymers of the invention possess significantly greater hardness.

EXAMPLE 5

A prepolymer is prepared according to the procedure in Example 1 using methanol as the solvent rather than tetrahydrofuran. A two part dental system is prepared as follows:
Part A:
  Prepolymer (from above)—20.0 parts
  Benzoyl peroxide—0.30 part
  Butylated hydroxytoluene—0.004 part
  Bisphenol A—0.024 part
  Ground barium glass (about 8 micron average size; silane-treated)—72.0 parts
Part B:
  Prepolymer (from above)—20.0 parts
  N,N-bis(hydroxyethyl)-p-toluidine—0.60 part
  2-(2'-hydroxy-5-methylphenyl)-benzotriazole—0.1 part
  Ground barium glass (about 8 micron average particle size; silane-treated)—72.0 parts Approximately equal portions of pastes A and B are mixed and cured to hard solid in about 55 seconds from the start of mixing. The two parts are stable for prolonged periods when stored as parts of a kit.

EXAMPLE 6

A prepolymer is prepared as in Example 5 and formulated as indicated below:

Part A:
  Prepolymer—18.0 parts
  Triethylene glycol dimethacrylate—2.0 parts
  Benzoyl peroxide—0.30 part
  Butylated hydroxytoluene—0.004 part
  Bisphenol A—0.024 part
  Ground barium glass (silane-treated)—72.0 parts Part B:
  Prepolymer—20.0 parts
  N,N-bis(hydroxyethyl)-p-toluidine—0.60 part
  2-(2'-hydroxy-5-methylphenyl)-benzotriazole—0.1 g
  Ground barium glass (silane-treated)—72.0 parts When equal portions of pastes A and B are mixed, a hard solid is obtained 1.5 minutes after the start of mixing. When retained separately the two parts are stable for prolonged periods but react when mixed in equal proportions.

EXAMPLE 7

A two part dental filling system is prepared as described in Example 2. Cylindrical samples about 7 mm in diameter and 13 mm high are prepared by mixing equal parts of A and B pastes and curing the resulting samples overnight at 37° C. in suitable molds. Control samples using a commercial product are run at the same time in the same way. These samples are then immersed in distilled water at 37° C. and the compressive strength measured as a function of immersion time at various intervals.

| Time immersed | Control kg/cm² | Example 2 kg/cm² |
|---|---|---|
| 24 hours | 2.22 × 10³ | 2.12 × 10³ |
| 7 days | 2.23 × 10³ | 2.26 × 10³ |
| 28 days | 2.54 × 10³ | 2.40 × 10³ |
| 3 months | 2.43 × 10³ | 2.51 × 10³ |
| 8 months | 2.53 × 10³ | 2.86 × 10³ |

These results show the excellent hydrolytic stability and compressive strength of compositions of the invention.

EXAMPLE 8

A UV-curable dental composition is prepared from
  5.0 parts—prepolymer of Example 1
  1.0 part—triethyleneglycol bismethacrylate
  0.16 part—benzoin isobutyl ether
  14.0 parts—ground barium glass.

The materials are mixed thoroughly. A small portion is removed and exposed to ultraviolet light from a device used for ultraviolet curing of dental restoratives for one minute. The material becomes very hard and appears to be as hard as other compositions of the invention.

What is claimed is:

1. An oligomeric prepolymer of the structure

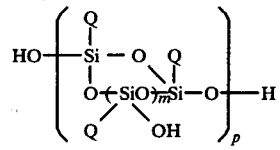

wherein
  each m is independently 1, 2 or 3,
  p is 2 to about 10,
  Q is $CH_2=C(CH_3)CO-X(CR_2)_n-$,
  X is O, S or NR,
  each R is independently hydrogen or lower alkyl of 1 to 2 carbon atoms and no more than two are lower alkyl and
  n is 3 to 12.

2. An oligomeric prepolymer according to claim 1 wherein X is O.

3. An oligomeric prepolymer according to claim 1 of the structure:

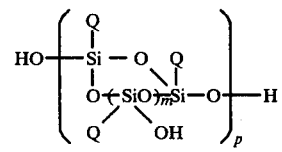

wherein
  Q is $CH_2=C(CH_3)CO-O(CH_2)_3-$
  p is 2 to about 10 and
  each m is independently 1, 2 or 3.

4. A process for producing a purified methacryl substituted alkyltrialkoxysilane of the formula

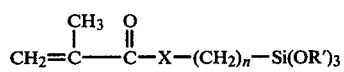

wherein
  X is O, S or NR,
  n is 3 to 12,
  each R is independently H or lower alkyl of 1–2 carbon atoms and no more than two are lower alkyl
  R' is unsubstituted lower alkyl of 1–4 carbon atoms said purified methacryl substituted alkyltrialkoxysilane characterized by being substantially colorless and free from contaminants and inhibitors to the extent that an exotherm with substantial increase in viscosity or gelation occurs within 20 minutes at ambient temperatures ater thorough mixing of approximately equal portions to which have been added, respectively, 1.5% by weight benzoyl peroxide and 3.0% by weight, N,N-bix(hydroxyethyl)-p-toluidine, comprising the successive steps of (1) stirring a methacryl substituted alkyltrialkoxysilane at above 100° C. for about 4 hours with about 10% by weight of anhydrous non-nucleophilic base followed by (2) stirring at ambient temperatures for about 1 hour with less than 1% of massive inorganic nucleophilic base and, after separation from solids residues, (3) distillation under reduced pressure to provide said purified methacryl substituted alkyltrialkoxysilane.

* * * * *